US011192780B1

(12) United States Patent
Biaggi-Labiosa et al.

(10) Patent No.: US 11,192,780 B1
(45) Date of Patent: Dec. 7, 2021

(54) TEMPLATED NANOSTRUCTURE SENSORS AND METHODS OF MANUFACTURE

(71) Applicant: United States of America as represented by the Administrator of NASA, Washington, DC (US)

(72) Inventors: Azlin M. Biaggi-Labiosa, North Ridgeville, OH (US); Gary W. Hunter, Oberlin, OH (US)

(73) Assignee: United States of America as Represented by the Administrator of National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 16/363,169

(22) Filed: Mar. 25, 2019

Related U.S. Application Data

(63) Continuation of application No. 13/788,041, filed on Mar. 7, 2013, now Pat. No. 10,294,099.

(60) Provisional application No. 61/614,583, filed on Mar. 23, 2012.

(51) Int. Cl.
 B81C 1/00 (2006.01)
(52) U.S. Cl.
 CPC .............................. B81C 1/00341 (2013.01)
(58) Field of Classification Search
 CPC ................................................ B81C 1/00341
 See application file for complete search history.

(56) References Cited

U.S. PATENT DOCUMENTS

| | | | |
|---|---|---|---|
| 6,194,066 | B1 | 2/2001 | Hoffman |
| 7,211,143 | B2 | 5/2007 | Yang et al. |
| 7,276,389 | B2 | 10/2007 | Kim et al. |
| 7,306,828 | B2 | 12/2007 | Barrera et al. |
| 7,355,216 | B2 | 4/2008 | Yang et al. |
| 7,465,210 | B2 | 12/2008 | Kim et al. |
| 7,592,039 | B2 | 9/2009 | Huang et al. |
| 7,713,778 | B2 | 5/2010 | Li et al. |
| 7,898,005 | B2 | 3/2011 | Yang et al. |
| 2008/0054790 | A1 | 3/2008 | Kim et al. |
| 2009/0017197 | A1 | 1/2009 | Zang |

(Continued)

OTHER PUBLICATIONS

Huang, J., et al. "Nanotubular SnO2 templated by cellulose fibers: synthesis and gas sensing." Chemistry of materials 17.13 (2005): 3513-3518.*

(Continued)

*Primary Examiner* — Robert J Eom
(74) *Attorney, Agent, or Firm* — Robert H. Earp, III; Mark Wolfgang; Helen M. Galus

(57) ABSTRACT

A microsensor and its method of manufacture are disclosed based on templated metal or metal oxide nanostructures. The microsensor includes an electrode that in one embodiment may be configured as a first sawtooth patterned electrode having a series of first peaks and first valleys and a second electrode that by be configured as a second sawtooth patterned electrode having a series of second peaks and second valleys where the second peaks generally align with the first peaks of the first electrode. A plurality of templated metal or metal oxide nanostructures connect on one side to the first electrode and on another side to the second electrode, where an electrical property of the microsensor changes in response to exposure to an environment to be monitored.

20 Claims, 13 Drawing Sheets

(56) References Cited

U.S. PATENT DOCUMENTS

2009/0157165 A1 6/2009 Miller et al.
2009/0213369 A1 8/2009 Lee et al.
2009/0319032 A1 12/2009 Weber et al.
2010/0006148 A1 1/2010 Zheng et al.
2011/0168968 A1 7/2011 Yang et al.
2011/0297541 A1 12/2011 Jayatissa et al.

OTHER PUBLICATIONS

Evans, Laura J., et al. "Controlled fabrication of nanostructure material based chemical sensors." MRS Online Proceedings Library Archive 1253 (2010).*
Vander Wal, Randy L., et al. "Synthesis methods, microscopy characterization and device integration of nanoscale metal oxide semiconductors for gas sensing." Sensors 9.10 (2009): 7866-7902. (Year: 2009).*
Satishkumar, B.C., et al., "Synthesis of material oxide nanorods using carbon nanotubes as templates" Journal of Materials Chemistry 10.9 (2000): 2115-2119.
Liu Jun-feng, et al. "Vanadium pentoxide nanobelts: hightly selective and stable ethanol sensor materials" Advanced Materials 176 (2005): 764-767.

\* cited by examiner

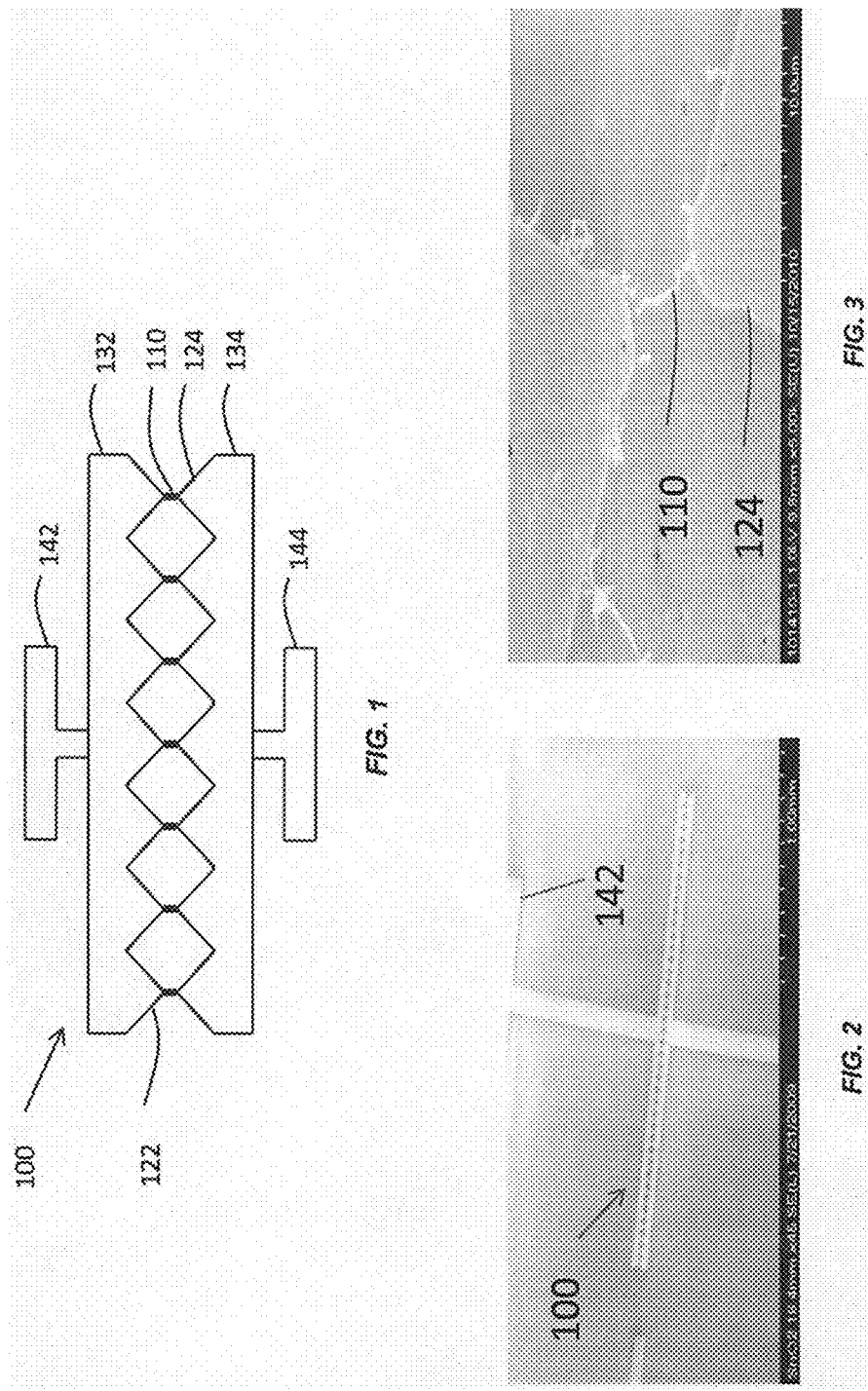

FIG. 4
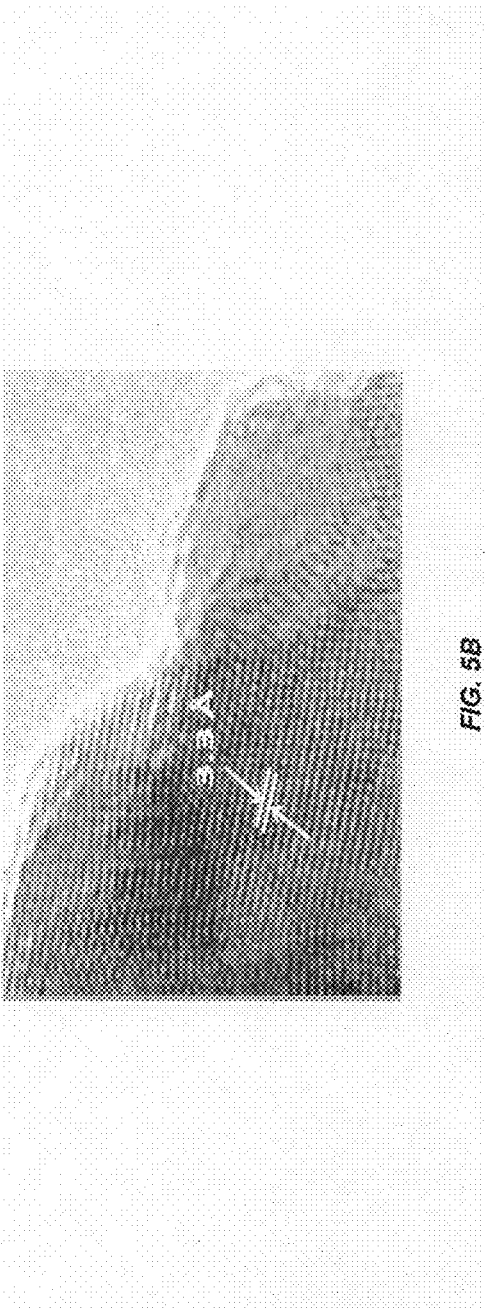
FIG. 5A
FIG. 5B

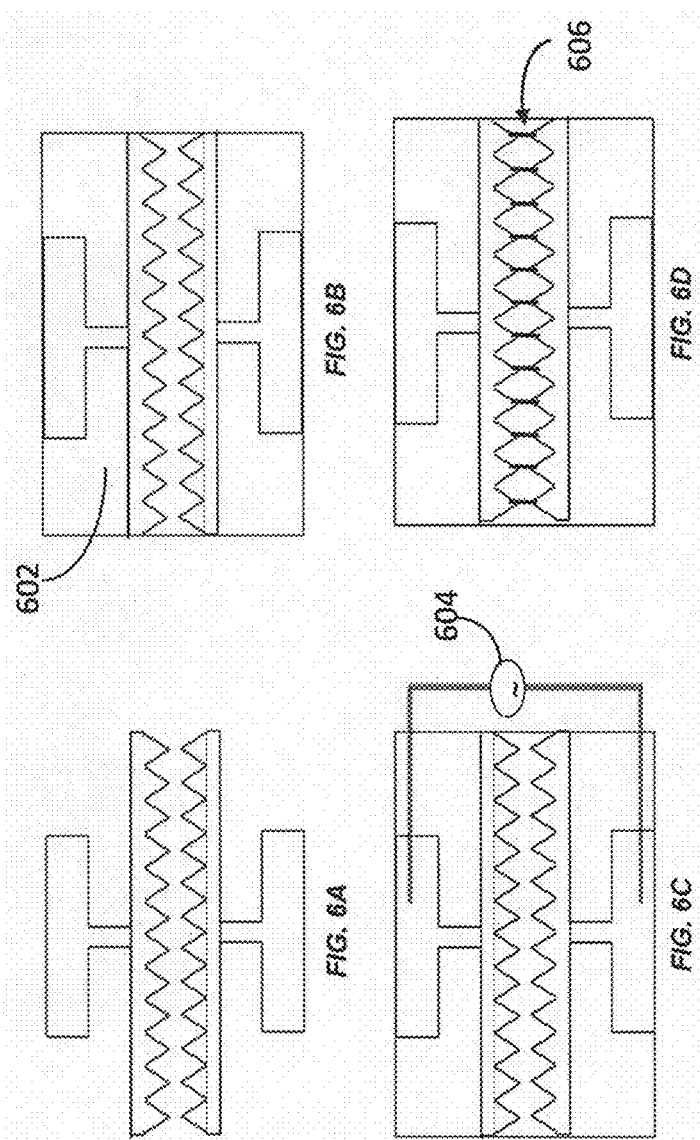

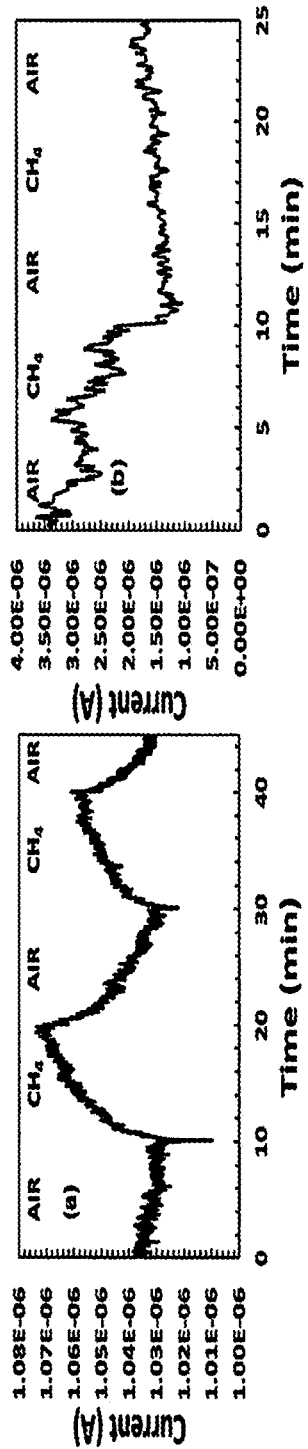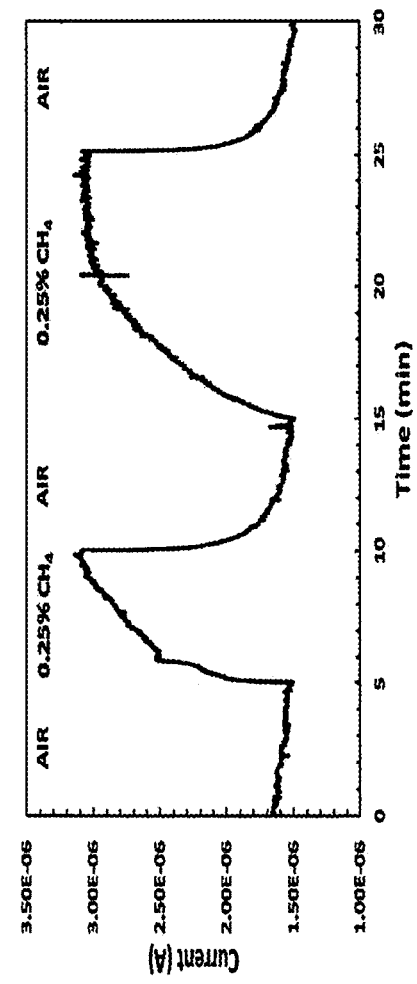
FIG. 8A
FIG. 8B
FIG. 9

TEMPLATED NANOSTRUCTURE SENSORS AND METHODS OF MANUFACTURE

CROSS-REFERENCE TO RELATED APPLICATIONS

This application is a Continuation Application claiming the benefit of priority from U.S. patent application Ser. No. 13/788,041 filed on Mar. 7, 2013, which claims the benefit of U.S. Provisional Application No. 61/614,583 filed on Mar. 23, 2012.

ORIGIN OF THE INVENTION

The invention described herein was made by an employee of the United States Government and may be manufactured and used by or for the United States Government for United States Government purposes without the payment of any royalties thereon or therefore.

DESCRIPTION

Chemical sensors are used in a wide variety of applications, including environmental monitoring, fire detection, emissions monitoring, and health monitoring. The fabrication of chemical sensors involving nanostructured materials holds the potential for the development of sensor systems with unique properties and improved performance. Semiconducting metal oxides like tin oxide ($SnO_2$) have been shown to respond to relevant chemical species such as oxygen ($O_2$), carbon monoxide (CO), ethanol ($C_2H_5OH$), nitric oxides ($NO_x$), propylene ($C_3H_6$), and hydrogen ($H_2$). There are a number of advantages to improving the capabilities of sensor materials such as metal oxides. For example, gas sensors based on polycrystalline tin oxide offer advantages over current technologies for detecting reducing gases, such as low cost, long lifetime, and high selectivity and sensitivity. The sensing mechanism in semiconducting metal oxides relies on perturbations in surface conductivity induced by chemical reactions between target gases and oxygen species adsorbed onto the surface. For n-type semiconductors like $SnO_2$, the adsorption of oxygen creates surface-acceptor sites that immobilize conduction band electrons from the near surface region creating a depletion layer. Reducing gases such as CO remove surface bound oxygen atoms releasing the immobilized electrons, thereby decreasing the thickness of the depletion layer and hence increasing its conductivity. In contrast, oxidizing gases (e.g. $NO_2$) further immobilize the conduction band electrons from the near surface region by creating additional surface-acceptor sites. This increases the thickness of the depletion layer and consequently, the conductivity decreases (in other words, resistance increases).

Moreover, the sensitivity of the sensing layer increases with decreasing grain size, therefore nanocrystalline metal oxides films exhibit high sensitivity. However, the processing and fabrication of nanostructures, such as nanotubes, nanowires, or other more complex geometries based on nanosystems, for sensor applications presently is limited in the ability to control the structural and morphological properties. In addition, one of the main drawbacks of semiconductor metal oxide based sensors is their high working temperature; the optimum operating temperature is usually at least 350-450° C. In general, we have found it is desirable to produce sensors which are small in size, easy to batch fabricate, are low in cost, and have low power consumption. We also sought to decrease the operational temperature of existing gas sensor systems to allow lower temperature operation as well as increased sensitivity and selectivity.

The accompanying drawings, which are incorporated in and constitute a part of the specification, illustrate various example systems, methods, and so on that illustrates various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DESCRIPTION OF DRAWINGS

FIG. 1 is a top plan view of a sensor according to an aspect of the disclosure.

FIG. 2 is a scanning electron microscope image of a microsensor.

FIG. 3 is a scanning electron microscope image of a templated $SnO_2$ nanorod between opposing electrode peaks.

FIG. 4 is a transmission electron microscope image of a carbon nanorod covered in a metal oxide.

FIG. 5A is a transmission electron microscope image of a templated $SnO_2$ nanorod.

FIG. 5B is a high resolution transmission electron microscope image of a templated $SnO_2$ nanorod.

FIGS. 6A-6D are sequential figures showing aspects of sensor fabrication.

FIGS. 8A-8B are comparison charts of sensor performance.

FIG. 9 is a chart of sensor performance.

Figure 7A:
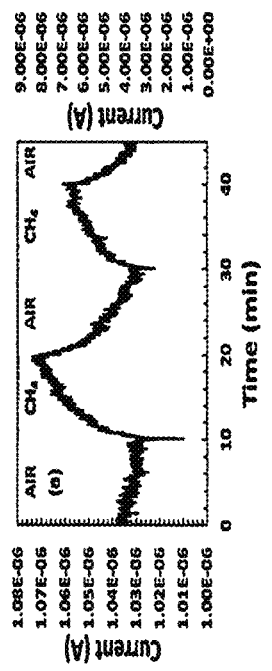
FIGS. 7A-7F are comparison charts of templated sensor performance at varying temperatures.
Figure 7B:
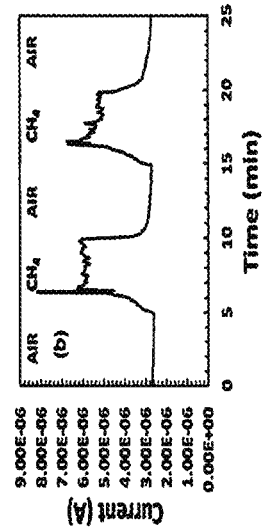
Figure 7C:
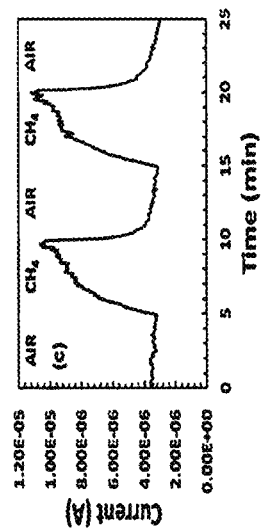
Figure 7D:
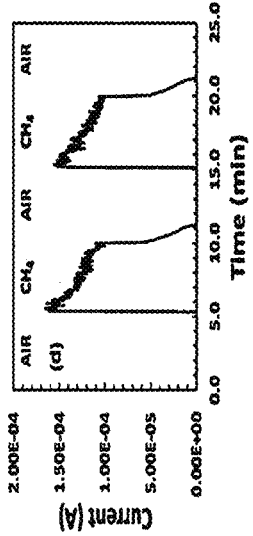
Figure 7E:
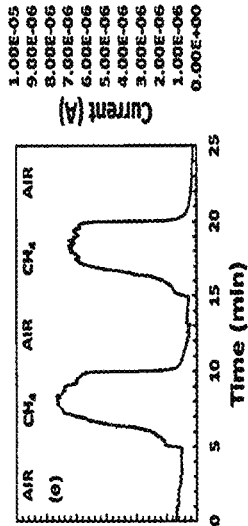

As used herein, the term "templated" or "templated nanostructure" is intended to describe a resulting nanostructure formed from an initial template that has a morphological structure that is then coated by a higher temperature material. The initial template is sacrificed leaving essentially only the higher temperature material imprinted with the morphological structure of the template.

One example we considered was the sensitive detection of methane, which is a colorless and odorless flammable gas that occurs abundantly in nature as the chief constituent of natural gas. Methane gas is highly volatile and when mixed with air can cause explosions at higher concentrations due to its ready flammability. Thus, the development of a reliable and cost effective methane gas sensor was a promising problem for timely detection of its conspicuous presence in the environment around us. However, detection of methane at room temperature using a number of techniques is a particularly difficult challenge because it is a stable molecule. Efforts have been made to detect methane at room temperature using material systems such as single walled carbon nanotubes and multi walled carbon nano tubes (MWCNTs) loaded with a catalyst such as palladium (Pd), and a Batron phosphorus-silicon microsensor, but they lack the temperature range and durability of materials such as metal oxides or metals.

A room temperature methane microsensor based on templated $SnO_2$ nanorods has been developed. The sensor may be fabricated by combining microfabrication techniques with the alignment of the nanostructures such as described in the U.S. patent application Ser. No. 13/036,887 entitled "Processing of Nanostructured Devices using Microfabrication Techniques" assigned to the assignee of the present disclosure and incorporated herein by reference and used in the following description of the sensor element (but not sensor material(s)) fabrication. The templated $SnO_2$ nanorods may be synthesized using carbon nanotubes as templates. As will be more fully described below, we have here described a sensor that operated at room temperature and detection of 0.25% methane in air. Furthermore, the uniqueness of this templated $SnO_2$ nanorod sensor includes the fact that it has a wide operating temperature range for $CH_4$ detection (25-500° C.), in contrast with the other material systems described above. Although tested on methane, hydrogen and propylene, the microsensor is expected to perform in other gaseous environments including those with hydrocarbon gases, carbon monoxide, nitrogen oxides, nitrogen tetraoxide, flourines, chlorines, ammonia, hydrazine, formaldehyde and in aqueous environments. Moreover, other templates beyond carbon nanotubes may be substituted to achieve the desired template features of the remaining nanotubes and corresponding sensitivity. These include, but are not limited to, biological materials such as plants, cells, filtration materials, organic substrates, and other materials whose basic structure holds biological advantages, but have a limited temperature range before undergoing decomposition. Other approaches have used a basic template approach. For example, sacrificial fibers can be coated with a metal to achieve modified sensor surface areas, or ceramic surfaces can serve as a basic structure for etching, growth, or modification to produce metal structures. However, these approaches are not based inherently on imprinting the crystal structure or inherent morphological properties of the substrate for improved sensing capabilities. Further, other oxide materials known for their gas sensing capabilities beyond tin oxide may be considered for the application of this approach. These include, but are not limited to tungsten oxide, titanium dioxide, indium oxide, indium tin oxide, zirconia, zinc oxide, copper oxide and iron oxide. Further, this approach may also be extended into metals that are known for their gas sensing capabilities. These include, but are not limited to, platinum, palladium, nickel, gold, ruthenium, silver, and iridium.

In one aspect, existing nanostructures such as carbon nanotubes have a material structure which can be used advantageously in order to provide new sensor systems. In a method of manufacturing, a user may start with a nanostructure template such as a carbon nanotube. This template can then be coated by a metal or oxide material with higher temperature capabilities. Upon heating in air, the carbon nanotube template is burned off leaving only the metal or metal oxide coating that retains the form of the carbon nanotube template. The resulting structure has a combination of the crystal patterns and surface morphology of the carbon nanotube, combined with the material durability and high temperature sensing properties of the metal or metal oxide. Further, because of its porosity, both the interior and the exterior of this sensing structure are available for gas species detection. This in effect increases the surface area available for sensing.

The limited capability to control the structural and morphological properties of nanostructures constraints their use in the processing and fabrication for sensor applications. For example, fabrication of sensors based on metals or metal oxides typically takes place in a growth process that yields a single or multi-grained structure with a structure determined by the crystallographic properties of the oxide. The surface area and morphology of such metals or metal oxides are notably different than that of, for example, other materials such as carbon nanotubes. In contrast, carbon nanotubes are noted for their large surface area and reactivity due in part to the crystal structure and resultant morphology. In principle, there could be notable advantages in producing metal or metal oxide nanostructures with a surface area and morphology similar to that of carbon nanotubes. However, it is considerably challenging to fabricate metal or metal oxide nanostructures with the same advantageous surface area and morphology, and potentially sensing properties, as carbon nanotubes. In effect, given the challenges in growing metal oxides and other materials such as metals, controlling and designing the material structure and morphology is problematic. One fundamental problem being addressed is improving the control of the structural and morphological properties of metal oxide and metal nanostructures in order to produce improved sensor systems.

In one example shown at FIGS. 1-3, a room temperature methane ($CH_4$) microsensor 100 based on templated tin oxide nanotubes 110 has been developed. The sensor 100 was fabricated integrating microfabrication techniques with the alignment and connection of the nanostructures between opposed tips 122, 124 of electrodes, 132, 134. As more completely discussed below, templated tin oxide nanorods 110 were fabricated using carbon nanotubes as templates. The sensor 100 has been operated at a room temperature and detection of 0.25% methane in air demonstrated. The room temperature methane microsensor has the advantages of low power consumption, no heating requirement, and only using a detector (not shown) for changes in the sensor, such as electrical changes in resistance or conductance between electrode pads 142, 144. The sensor is small in size, simple to batch fabricate and high in sensor yield, extremely low cost, and easy to use. Again, while tested on methane ($CH_4$), the microsensor is expected to perform in other gaseous environments and in aqueous environments. Moreover, other templates beyond carbon nanotubes may be substituted to achieve the desired template features of the remaining metal or metal oxide nanotubes. Finally, while the nanotube alignment between opposing saw-tooth elements of electrodes is illustrated, many other configurations are possible where the template nanotubes provide a connection between opposed electrodes. In one embodiment, it is the change in material properties enabling enhanced sensing capabilities that is desirable as opposed to a specific fabrication approach which makes contact with these nano structured materials.

Example

In one example, fabrication of a microsensor included four major steps: 1) synthesis of templated metal or metal oxide nanostructures using a sacrificial template; 2) deposition of electrodes onto an alumina substrate; 3) alignment of the nanostructures between the electrodes and 4) deposition of the top electrodes to bury the aligned nanostructures.

Templated $SnO_2$ nanorods were synthesized using multi-walled carbon nanotubes (MWCNT) as templates. First, 1.0 g of MWCNT obtained commercially from NanoLab was refluxed in 100 mL of 7.0 M $HNO_3$ for 12 hours at 120° C. to remove any impurities from the nanotubes and to create oxygen-containing functional groups on the nanotube surface that act as sites for the subsequent $SnO_2$ coating. 1.0 g of $SnCl_2.2H_2O$ was dissolved in 40 mL of deionized water and 0.25 mL of 38% HCl was added. Next, 10 mg of the purified MWCNT was added and the solution was sonicated for 20 minutes. Afterwards, the solution was stirred at room temperature for 2 hours and then rinsed with deionized water until the solution was neutral. At this point, $SnO_2$/MWCNT hybrid nanostructures are obtained. FIG. 4 illustrates a MWCNT covered with $SnO_2$ nanoparticles, 400. The $SnO_2$/MWCNT hybrid nanostructures were then calcinated at 350° C. for 3 hours and then heated at 700° C. for 5 minutes to burn off the MWCNT. FIG. 5A shows the templated $SnO_2$ nanostructures, 500, formed as nanorods. FIG. 5B shows a high resolution transmission electron microscope (HRTEM) image of the nanocrystals in the templated $SnO_2$ nanorod with the lattice spacing corresponding to the rutile structure of $SnO_2$.

After obtaining the templated $SnO_2$ nanorods, the challenge is to integrate the nanostructures into a micro/macro sensor. Usually doing this involves repeatability issues as well as poor control of the density of the nanomaterial. The basic ability to control the orientation and alignment of nanostructures on microstructures is still in an early stage of development although various groups have made significant progress on a range of materials. In our example, this has been overcome by fabricating the sensors using microfabrication techniques combined with the alignment of the nanostructures using dielectrophoresis (DEP). As illustrated in FIG. 6, alumina substrates were patterned with a sawtooth electrode pattern with contact pads through photolithography and 2500 Å of platinum was deposited by sputter deposition, FIG. 6A. The templated $SnO_2$ nanorods are added to a photoresist solution 602 which is coated onto the substrate with the patterned electrodes, FIG. 6B. Dielectrophoresis is then used by applying an alternate current, 604, with a frequency of 10 MHz and 10 V peak to peak, through the contact pads in the substrate to align the templated $SnO_2$ nanorods 606 between the sawtooth patterned electrodes, FIGS. 6C and 6D. Afterwards, a top platinum electrode is patterned through photolithography and sputter deposited on top of the bottom platinum electrode. This way the templated $SnO_2$ nanorods are buried between the bottom and top electrodes.

The methane microsensor described has a variety of advantages over other room temperature methane sensors in the simple synthesis of the sensing material with a stable metal oxide material, and over high temperature methane sensors in many aspects, especially in power consumption (no heating, only an amperometer is needed). Other advantages include miniature size, low weight and cost, and convenience of use. This particular sensor example has other desirable attributes. First, is the use of microfabrication processes to fabricate microsized sensor electrodes. The application of photolithography and sputtering processing to fabricate sensor electrodes enables the sensor to have small sizes. The electrodes shown in FIGS. 2 and 3 comprise sawtooth patterned electrodes which would be very difficult to make with other processes. The electrodes are batch fabricated with low cost, high yield, and robust structure. However, one attribute is the use of templated $SnO_2$ nanorods and the design of the sensor structure that yields unique sensor properties.

The templated $SnO_2$ nanorods that were used as the sensing material are composed of a network of $SnO_2$ nanocrystals. When the $SnO_2$ crystallite size is comparable to or less than 2 L (~6 nm), where L is the depth of the depletion layer, the sensitivity can be greatly increased because the sensitivity of the sensor's transducer function is proportional to the surface to volume ratio of the sensor material. The size of the nanocrystals on the templated $SnO_2$ nanorods was measured to be on average ~5.0 nm.

When the templated $SnO_2$ nanorods described are used as the sensing material, because of their porous nature as illustrated in FIG. 5A, they become more sensitive than non-templated $SnO_2$ nanorods, nanobelts, nanocrystalline thin films or other nanostructures because gas molecules can freely pass into and out of the templated nanorod through the pores and interact with the outer as well as the inner surface of the nanorod. As a consequence, there is a larger effective area and the sensitivity at room temperature is greatly increased. However, the increase in active surface area and consequently, gas diffusion does not necessarily translate into a proportional increase in sensitivity. There are other factors involved in the transduction of the analyte gas/surface reactions into an electrical conductance change: 1) electrode/$SnO_2$ nanotube contact, 2) nanocrystal organization within the $SnO_2$ nanotube and 3) electrical and surface properties of the electrodes.

Furthermore, by having sawtooth patterned electrodes on the sensor structure, the use of DEP to align the nanostructures becomes more feasible. DEP exploits the dielectric difference between the solvent and the nanostructures in the solvent to induce temporary dipoles that align with the imposed electric field. Because of the geometry of the electrodes, the electric field is greater at the tips of the sawtooth patterned electrodes which accounts for the preferential alignment of the nanotubes between the tips of opposing sawtooth electrodes. The approach used also allows for the ability to bury the nanostructure by performing a second electrode deposition on top of the aligned nanostructure, as described previously, allowing improved electrical contact.

A set of comparison tests were conducted comparing five different types of sensors:

Sensors formed from multiwall carbon nanotubes (listed as MWCNT).

Sensors formed from single wall carbon nanotubes (listed as SWCNT).

Sensors formed from hybrid multiwall carbon nanotubes coated in $SnO_2$.

Sensors formed from hybrid single wall carbon nanotubes coated in $SnO_2$.

Sensors formed from templated $SnO_2$ nanotubes.

All sensors were tested for 0.5% $H_2$ and 0.5% $CH_4$ in air at 25° C., 100° C., 200° C. and 300° C. As can be seen from in Table 1 the templated $SnO_2$ nanotube sensors had improved sensitivity in all testing conditions for both gasses. The values given in the table are the ratio of the sensor response to the reactant gas to that of its response in air.

TABLE 1

| Structure | Sensor target | 25° C. | 100° C. | 200° C. | 300° C. |
|---|---|---|---|---|---|
| SWCNT | $H_2$ | 1.225 | N-M | 1.066 | 1.095 |
|  | $CH_4$ | N-M | N-M | 1.021 | 1.042 |
| MWCNT | $H_2$ | 1.0037 | N-M | N-M | N-M |
|  | $CH_4$ | N-R | N-R | N-R | N-R |
| $SnO_2$/MWCNT | $H_2$ | 1.089 | N-M | N-M | N-M |
|  | $CH_4$ | N-R | N-R | 1.001 | 1.001 |
| $SnO_2$/SWCNT | $H_2$ | 1.27 | N-M | 1.023 | 1.098 |
|  | $CH_4$ | N-M | N-R | 1.022 | 1.026 |

TABLE 1-continued

| Structure | Sensor target | 25° C. | 100° C. | 200° C. | 300° C. |
|---|---|---|---|---|---|
| Templated SnO$_2$ Nanotube | H$_2$ | 4.27 | 6.69 | 2.38 | 17.15 |
| | CH$_4$ | 1.34 | 1.18 | 1.24 | 3.65 |

N-M = Not measurable
N-R = No response

Figure 7F:
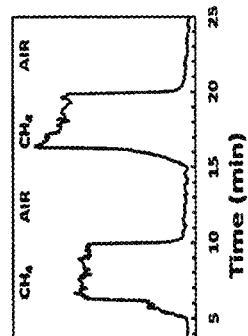

The sensor can be tested using the amperometric mode, by applying a voltage between the electrodes and measuring the current between them. In one example, FIG. 7 shows Current vs. Time curves were taken at different operating temperatures (25-500° C.) for sensors using templated SnO$_2$ nanorods as the sensing material for response to 0.25% CH$_4$ at the different temperatures where all measurements were taken with an applied voltage of 1.0 V and using air as the baseline gas. Shaded areas indicate "exposure" and correspond to the times of CH$_4$ gas exposure. As it can be seen, the templated SnO$_2$ nanorod sensor showed a measurable response to 0.25% CH$_4$ at room temperature (FIG. 7A) and continued response throughout the test up to 500° C. (FIG. 7F). In addition, as it can be appreciated in FIG. 7, the baseline at the different temperatures remains reasonably stable throughout the tests.

FIG. 8 shows a comparison test of a templated, porous SnO$_2$ nanorod sensor (FIG. 8A) and an alternative sensor structure using solid (non-templated) SnO$_2$ nanobelts without using the carbon nanotube-SnO$_2$ imprinting approach (FIG. 8B). Both Figures show Current vs. Time curves for 0.25% CH$_4$ in air at 25° C. and 1.0V. As can be seen, the non-templated sensor does not appear to show a usable response to CH$_4$ at room temperature.

FIG. 9 shows a sensor response curve to 0.25% CH$_4$ in air at 25° C. and 1.0V after approximately 190 hours of continuous testing of the templated SnO$_2$ nanorod sensor, cycling back and forth between the different temperatures. The curve shows an improved response to CH$_4$ at room temperature with little change in the baseline when compared with the previous results, thus establishing the sensor's long-term stability.

Figure 10:
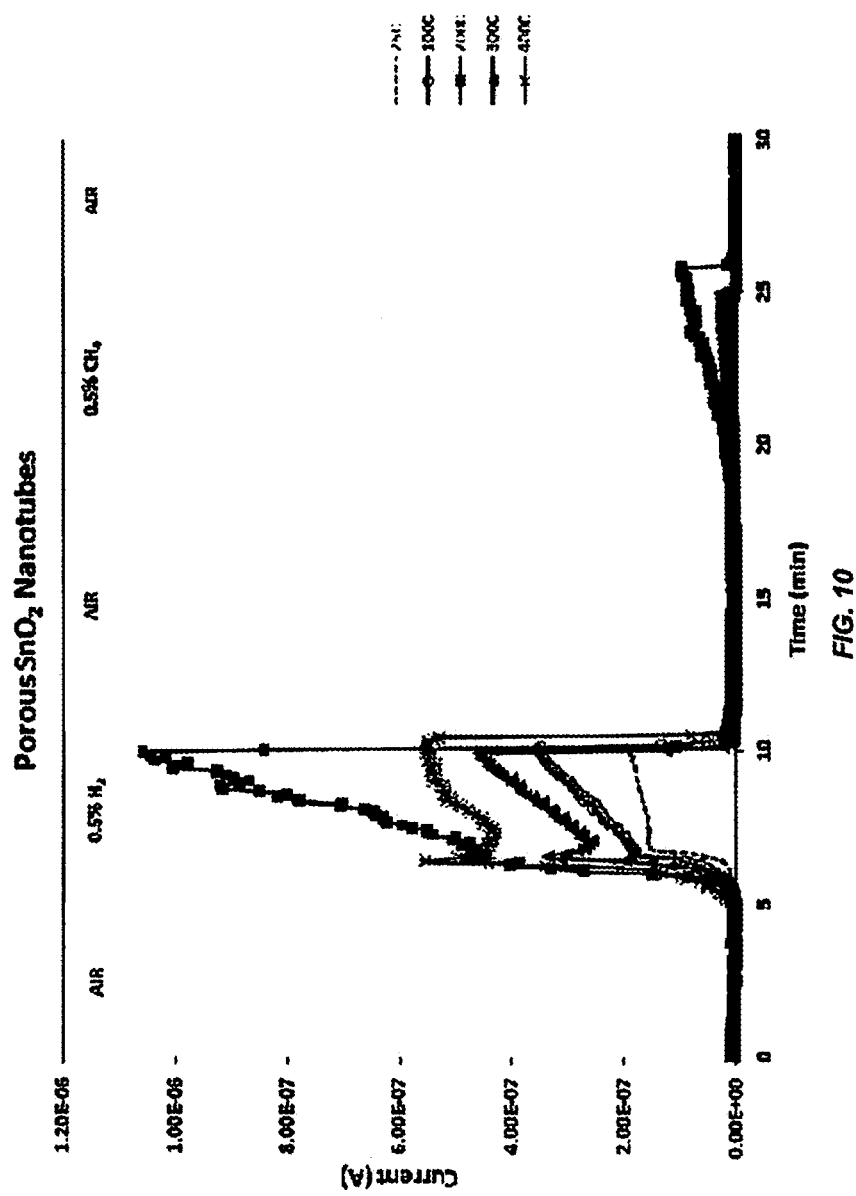
FIG. 10 is chart comparing sensor performance at varying temperatures.

FIG. 10 shows a templated SnO$_2$ nanotube sensor performance over time spaced exposures to 0.5% H$_2$ (during minutes 5-10) and 0.5% CH$_4$ (during minutes 18-26) in air at temperatures varying from 25° C. to 400° C.

Figure 11:
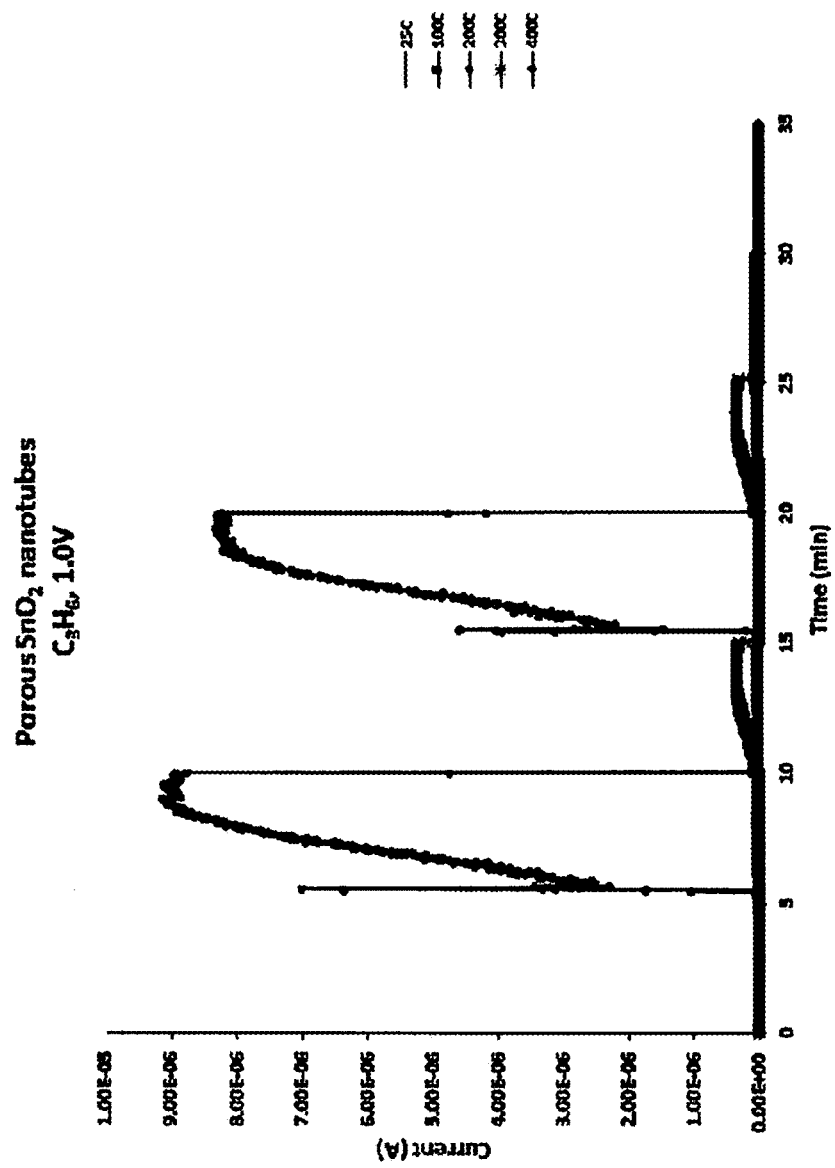
FIGS. 11-17 are charts showing sensor performance at varying temperatures.
Figure 12:
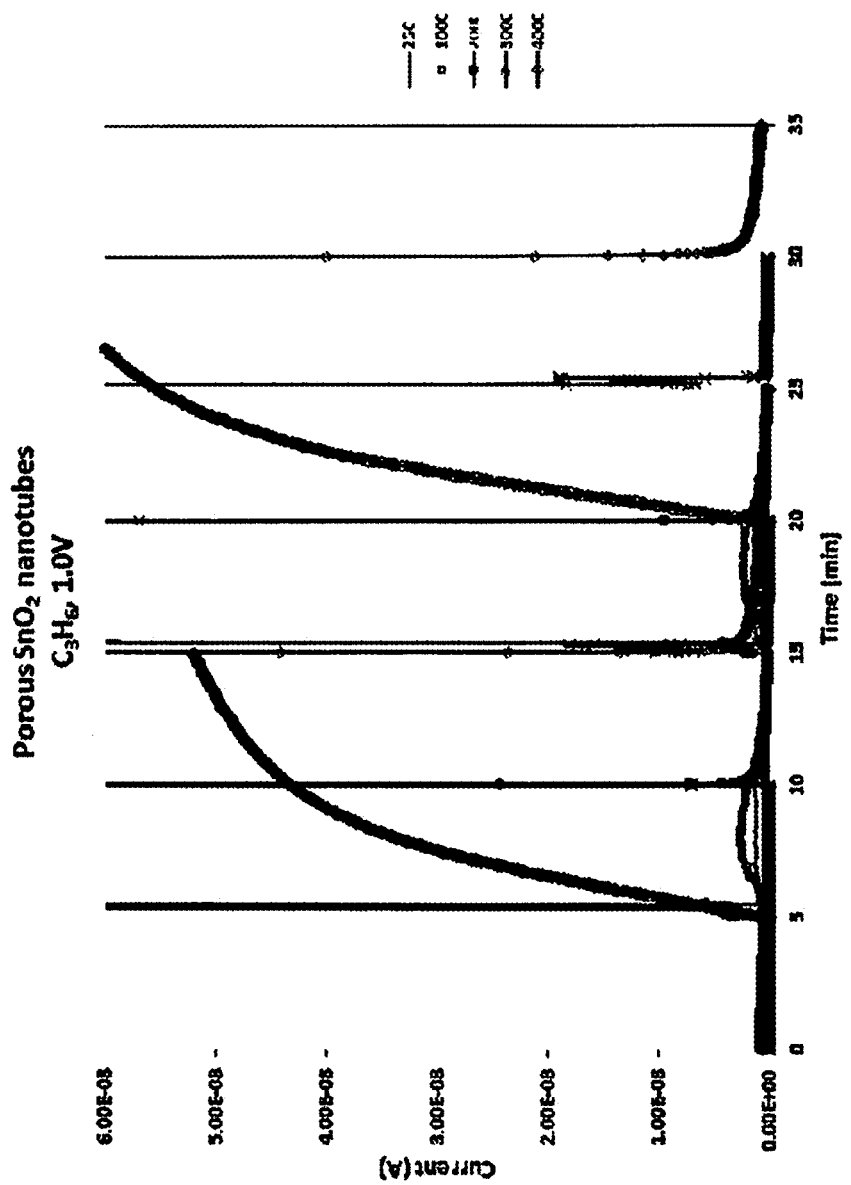

FIGS. 11 and 12 show a templated SnO$_2$ nanotube sensor performance over time spaced exposures to C$_3$H$_6$ sensor in air at temperatures varying from 25° C. to 400° C. at varying scales.

Figure 13:
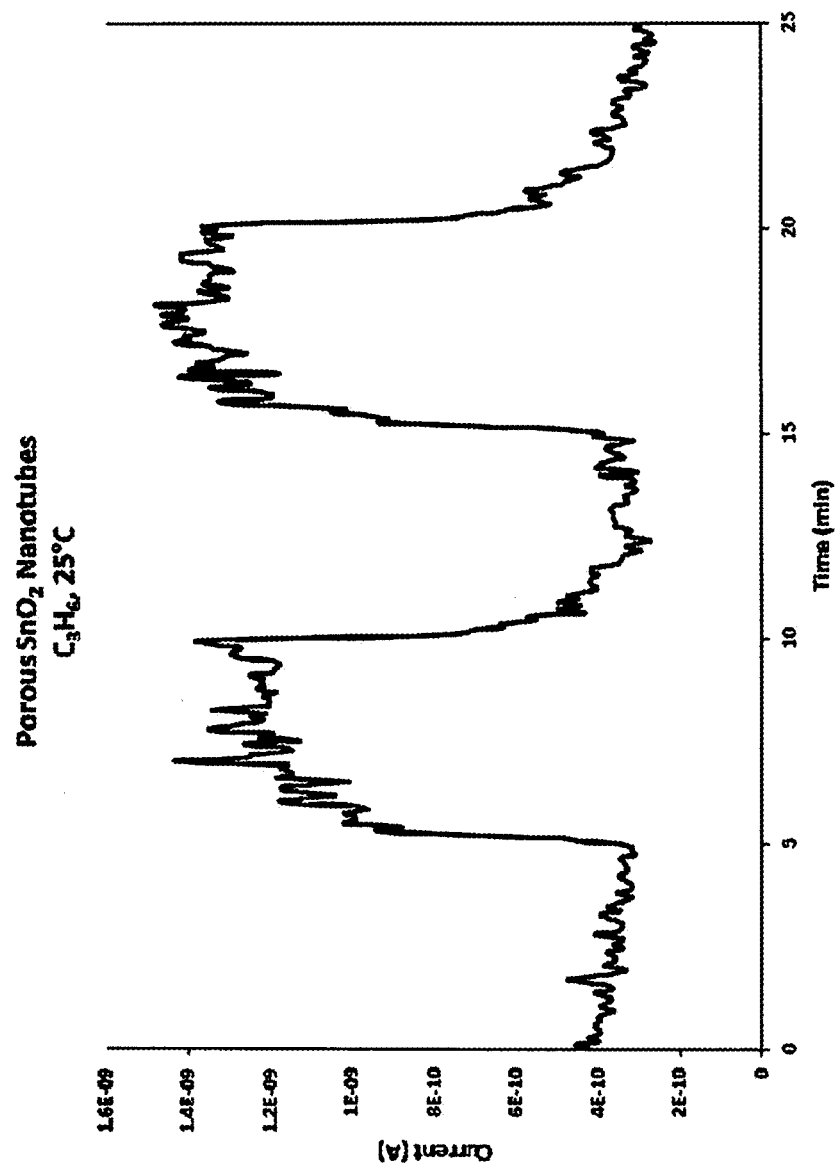
Figure 14:
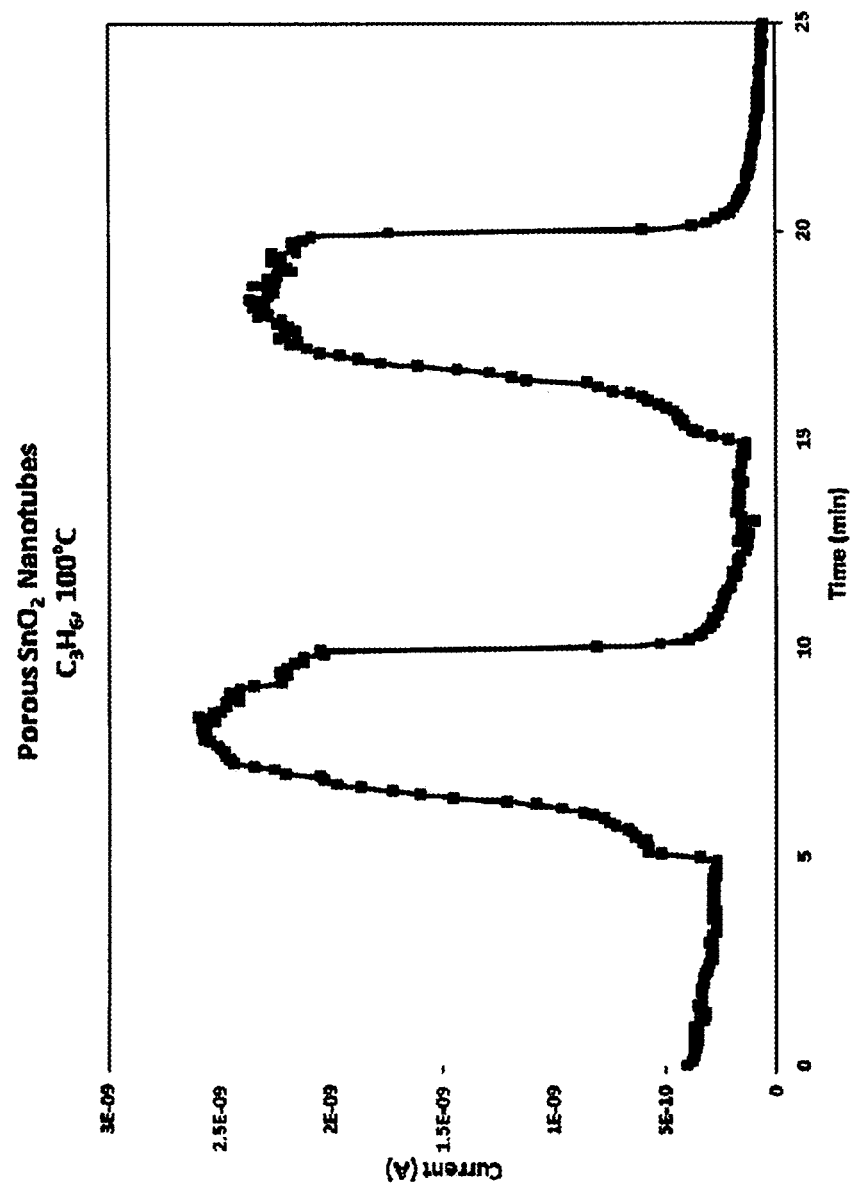
Figure 15:
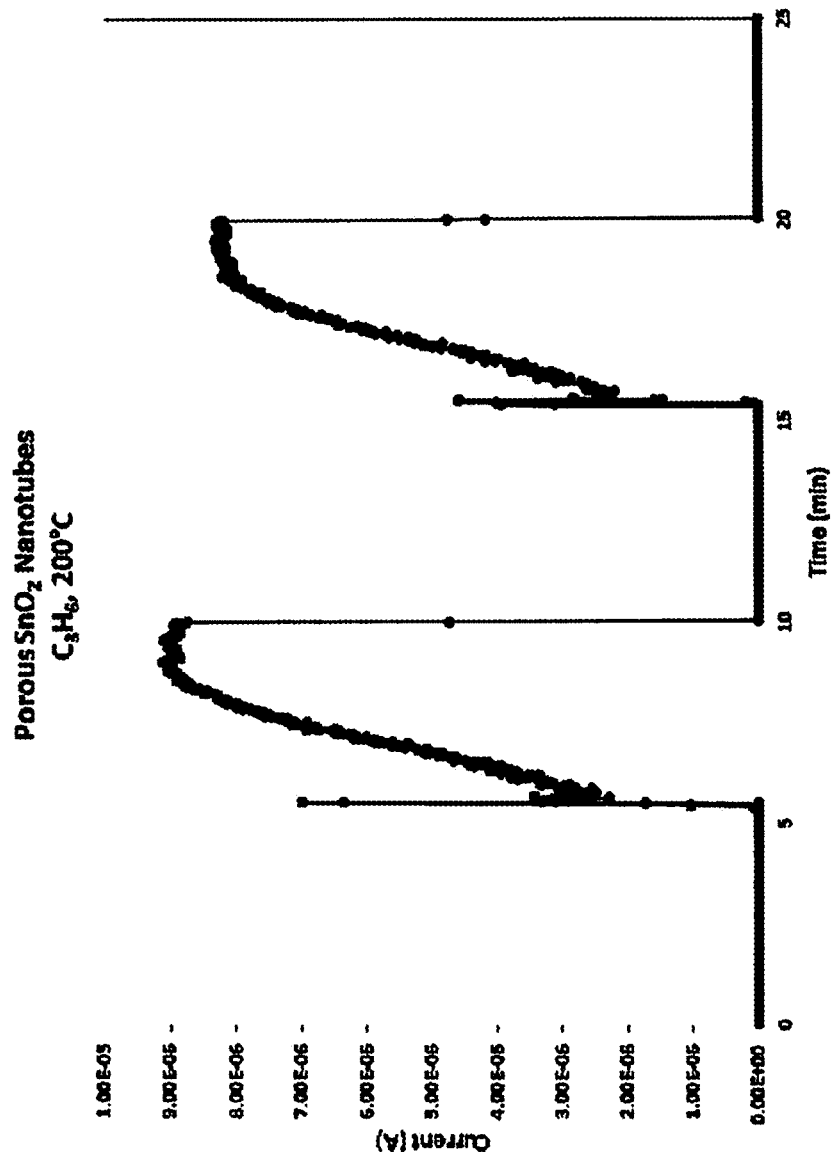
Figure 16:
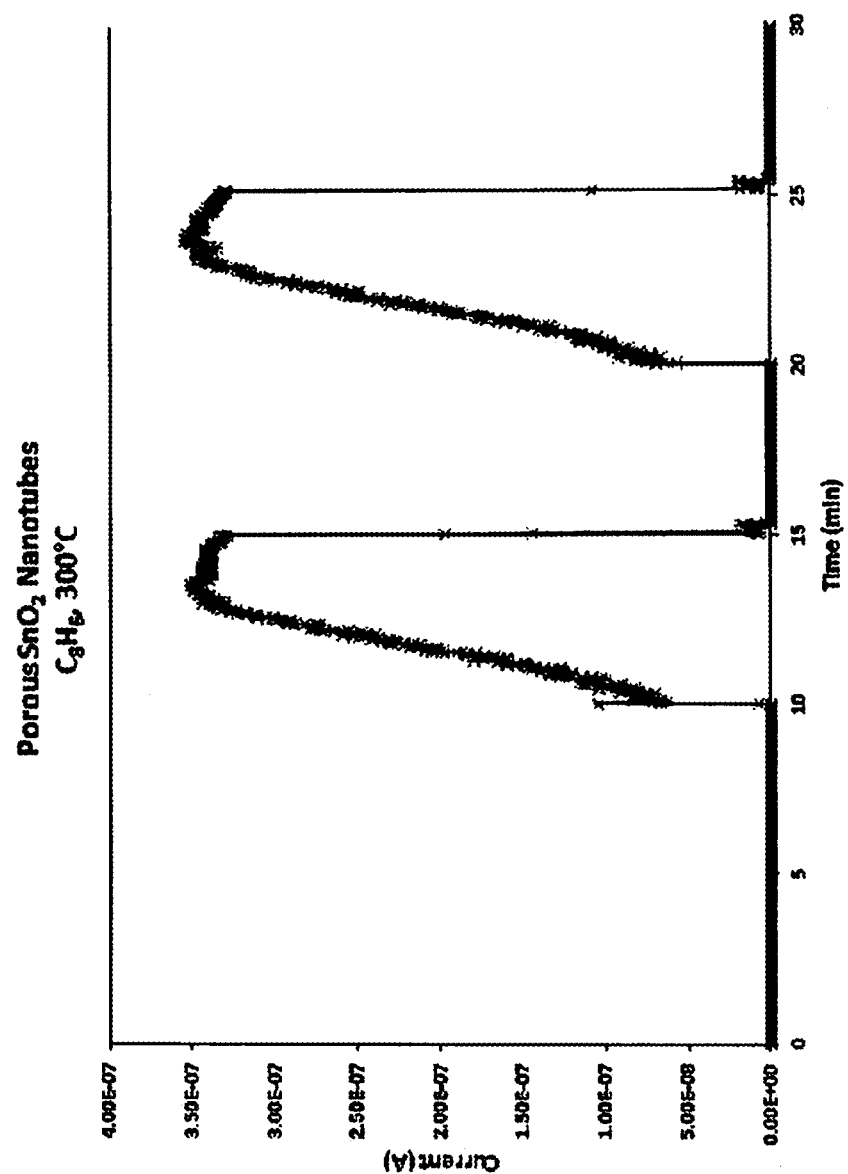
Figure 17:
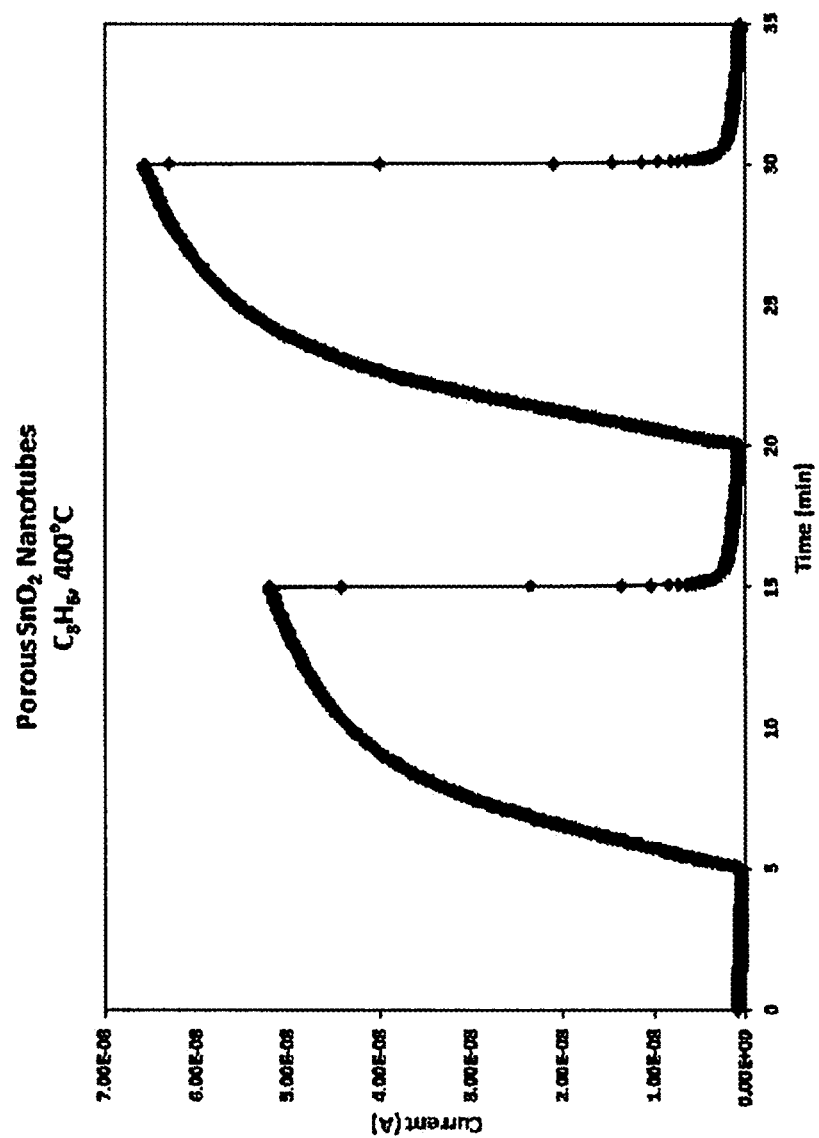

FIGS. 13 and 17 show the templated SnO$_2$ nanotube sensor performance of FIGS. 11 and 12 over time spaced exposures to C$_3$H$_6$ sensor in air at temperatures varying from 25° C. to 400° C. at varying scales.

While the systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on provided herein. Specific applications include toxic gas monitoring, explosive gas monitoring, detection of biological agents, and detection of biological molecules of interest such as cells, viruses, or proteins. A range of species are of interest to the scientific community and industry. One example can be found at http://www.nasa.gov/centers/johnson/pdf/485930main_S-MACsGuidelines.pdf Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicants' general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents. For example, although we describe sacrificing the "template" with high temperatures, one could also sacrifice with pressure or chemical solutions resulting in the templated nanostructure described. Moreover, other templates may be identified and selected for sensitivity to other desirable substances to test for in an air or liquid environment. Accordingly, the preceding description is not meant to limit the scope of the invention. Rather, the scope of the invention is to be determined by the appended claims and their equivalents.

As used herein, "connection" or "connected" means both directly, that is, without other intervening elements or components, as well as indirectly, that is, with another component or components arranged between the items identified or described as being connected. To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the claims (e.g., A or B) it is intended to mean "A or B or both". When the applicants intend to indicate "only A or B but not both" then the term "only A or B but not both" will be employed. Similarly, when the applicants intend to indicate "one and only one" of A, B, or C, the applicants will employ the phrase "one and only one". Thus, use of the term "or" herein is the inclusive, and not the exclusive use. See, Bryan A. Garner, A Dictionary of Modern Legal Usage 624 (2d. Ed. 1995).

The invention claimed is:

1. A microsensor comprising:
   a first electrode;
   a second electrode;
   a substrate, wherein the first electrode and the second electrode are deposited onto the substrate in a pattern;
   at least one templated nanostructure aligned between a tip of the first electrode and a tip of the second electrode, the at least one templated nanostructure defining opposed sides, where on one side the at least one templated nanostructure provides an electrical connection to the first electrode and on an opposed side the at least one templated nanostructure provides an electrical connection to the second electrode, and
   a top electrode deposited on the first electrode and the second electrode such that the at least one templated nanostructure is buried,
   wherein the at least one templated nanostructure comprises a metal oxide precipitate having a crystallite size, with crystal patterns and an interior surface imprinted with the morphological properties of a sacrificed structural template, the crystal patterns and interior surface morphological properties of the precipitate are used as a sensor via a depletion layer of the precipitate, wherein the crystallite size is less than twice a depth of the depletion layer of the precipitate, for sensing one or more selected contaminants, and where an electrical property of the microsensor changes in response to exposure to an environment.

2. The microsensor as set forth in claim 1, where the environment is air.

3. The microsensor as set forth in claim 1, where the electrical property of the microsensor changes in response to exposure to selected contaminants in the environment.

4. The microsensor as set forth in claim 3, where the selected contaminants include hydrocarbon-based molecules, hydrazine, formaldehyde, oxidizers, nitrogen oxides, nitrogen tetraoxides, fluorine, chlorines, or ammonia.

5. The microsensor as set forth in claim 3, where the selected contaminants include a reducing gas.

6. The microsensor as set forth in claim 1, where the environment is an aqueous solution.

7. The microsensor as set forth in claim 6, where the electrical property of the microsensor changes in response to exposure to biological molecules in the aqueous solution.

8. The microsensor as set forth in claim 1, where the microsensor includes a measurable response to $CH_4$ in air at 25° C.

9. The microsensor as set forth in claim 1, where the microsensor includes a measurable response to hydrocarbons in air between at least 25° C.-600° C.

10. The microsensor as set forth in claim 1, where the microsensor includes a measurable response to hydrogen in air from at least 25° C.-600° C.

11. The microsensor as set forth in claim 1, where the at least one templated nanostructure is selected from the set of tin oxide, tungsten oxide, titanium dioxide, indium oxide, indium tin oxide, zirconia, zinc oxide, copper oxide and iron oxide.

12. The microsensor as set forth in claim 1, where the at least one templated nanostructure comprises an imprint of a surface area of multiwall carbon nanotubes.

13. The microsensor as set forth in claim 1, where the at least one templated nanostructure comprises an imprint of a surface area of single wall carbon nanotubes.

14. The microsensor as set forth in claim 1, where the first electrode and the second electrode are patterned and aligned with one another.

15. The microsensor as set forth in claim 14, where the patterns of the first electrode and the second electrode comprise sawtooth patterns.

16. The sawtooth patterns as set forth in claim 15, where the at least one templated nanostructures are aligned between tips of the sawtooth patterns.

17. A microsensor comprising:
a first electrode;
a second electrode;
an alumina substrate, wherein the first electrode and the second electrode are deposited onto the alumina substrate in a pattern;
at least one templated nanostructure aligned between a tip of the first electrode and a tip of the second electrode, the at least one templated nanostructure defining opposed sides, where on one side the at least one templated nanostructure provides an electrical connection to the first electrode and on an opposed side the at least one templated nanostructure provides an electrical connection to the second electrode, and
a top electrode deposited on the first electrode and the second electrode to bury points of contact between the first electrode and the second electrode,
wherein the at least one templated nanostructure comprises a metal oxide precipitate, the metal oxide selected from the group consisting of: tin tungsten oxide, titanium dioxide, indium oxide, indium tin oxide, zirconia, zinc oxide, copper oxide, and iron oxide having a crystallite size, with crystal patterns and an interior surface imprinted with the morphological properties of a sacrificed structural template, the crystal patterns and interior surface morphological properties of the precipitate are used as a sensor via a depletion layer of the precipitate, wherein the crystallite size is less than twice a depth of the depletion layer of the precipitate, for sensing one or more selected contaminants, and where an electrical property of the microsensor changes in response to exposure to an environment.

18. The microsensor of claim 17, wherein the pattern of the first electrode and the second electrode comprise a sawtooth pattern.

19. The microsensor of claim 18, wherein the at least one templated nanostructure is aligned between tips of the sawtooth pattern.

20. The microsensor of claim 17, wherein the sacrificed structural template comprises a multiwalled carbon nanotube.

* * * * *